US012805813B2

(12) United States Patent
Wagner et al.

(10) Patent No.: US 12,805,813 B2
(45) Date of Patent: Nov. 24, 2026

(54) APPARATUS FOR X-RAY CT IMAGING WITH REDUCED PROBE ARTIFACTS

(71) Applicant: Wisconsin Alumni Research Foundation, Madison, WI (US)

(72) Inventors: Martin Wagner, Madison, WI (US); Timothy Peter Szczykutowicz, Madison, WI (US); Allison Couillard, Oconomowoc, WI (US); Fred Lee, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 286 days.

(21) Appl. No.: 18/411,131

(22) Filed: Jan. 12, 2024

(65) Prior Publication Data

US 2025/0228507 A1 Jul. 17, 2025

(51) Int. Cl.
*A61B 6/02* (2006.01)
*A61B 6/03* (2006.01)

(52) U.S. Cl.
CPC .............. *A61B 6/027* (2013.01); *A61B 6/025* (2013.01); *A61B 6/035* (2013.01)

(58) Field of Classification Search
CPC ... A61B 6/025; A61B 6/027; A61B 2090/376; A61B 2090/3762; A61B 2090/3764; A61B 6/035
See application file for complete search history.

(56) References Cited

U.S. PATENT DOCUMENTS

2007/0100234 A1* 5/2007 Arenson ................ A61B 6/032 600/429
2008/0091101 A1* 4/2008 Velusamy .......... A61B 10/0233 600/427
2009/0281452 A1* 11/2009 Pfister .................. A61B 6/5229 600/567
2010/0063514 A1* 3/2010 Maschke .............. A61B 5/1135 606/130
2010/0290583 A1* 11/2010 Noordhoek ............ A61B 6/547 378/4
2015/0196260 A1* 7/2015 Lee .......................... A61B 6/12 600/424
2016/0302871 A1* 10/2016 Gregerson ............. A61B 34/20
2017/0332983 A1* 11/2017 Tai .......................... A61B 6/037
2017/0354387 A1* 12/2017 Mc Carthy ........ A61B 17/3403
2018/0146933 A1* 5/2018 Lerch ..................... A61B 6/032
2018/0308247 A1* 10/2018 Gupta ................ A61B 10/0233
2019/0038245 A1* 2/2019 Bailey .................... A61B 6/035
2019/0038365 A1* 2/2019 Soper ..................... A61B 34/20

(Continued)

OTHER PUBLICATIONS

Kim et al.; "An additional tilted-scan-based CT metal-artifact-reduction method for radiation therapy planning." Journal of applied clinical medical physics 20, No. 1 (Sep. 2018): pp. 237-249. US.

*Primary Examiner* — David J Makiya
*Assistant Examiner* — Soorena Kefayati
(74) *Attorney, Agent, or Firm* — Boyle Fredrickson, S.C.

(57) ABSTRACT

Tomographic projection data is acquired in an acquisition plane angled with respect to a trajectory plane of a probe, such as a biopsy probe, to reconstruct an image in the trajectory plane, reducing probe-induced artifacts at the tip of the probe. Patient table position and angulation may be adjusted automatically and dynamically during probe insertion for this purpose.

16 Claims, 4 Drawing Sheets

(56) References Cited

U.S. PATENT DOCUMENTS

| | | | | |
|---|---|---|---|---|
| 2019/0110685 | A1* | 4/2019 | Pautsch | A61B 34/20 |
| 2020/0297377 | A1* | 9/2020 | Nields | A61B 17/3403 |
| 2021/0085211 | A1* | 3/2021 | Alexandroni | A61B 10/04 |
| 2021/0085268 | A1* | 3/2021 | Alexandroni | A61B 34/10 |
| 2021/0104055 | A1* | 4/2021 | Ni | A61B 34/20 |
| 2021/0169504 | A1* | 6/2021 | Brown | A61B 6/487 |
| 2021/0282862 | A1* | 9/2021 | Bourlion | A61B 34/10 |
| 2021/0330273 | A1* | 10/2021 | Crawford | A61B 6/4441 |
| 2022/0409148 | A1* | 12/2022 | Rose | A61B 6/035 |
| 2023/0015717 | A1* | 1/2023 | Wang | A61B 5/0077 |
| 2023/0146679 | A1* | 5/2023 | Lavallée | A61B 34/10<br>700/259 |
| 2023/0225684 | A1* | 7/2023 | Shen | A61B 6/12<br>600/424 |
| 2023/0355194 | A1* | 11/2023 | Gregerson | A61B 6/027 |
| 2023/0363828 | A1* | 11/2023 | Liu | A61B 6/08 |

* cited by examiner

APPARATUS FOR X-RAY CT IMAGING WITH REDUCED PROBE ARTIFACTS

STATEMENT REGARDING FEDERALLY SPONSORED RESEARCH OR DEVELOPMENT

Cross Reference to Related Application

Background of the Invention

The present invention relates generally to medical computed tomography (CT) and in particular to an x-ray CT machine operating to reduce artifacts associate with needle-like probes.

Many medical procedures utilize an introducer needle (cannula) that can be inserted through the skin of the patient of the patient to a target region for a specific intervention, for example, biopsy, injection, aspiration, drain placement, ablation, etc. During the insertion, a solid stylet maybe placed coaxially within the introducer needle to help to pierce the tissue and to help prevent coring of tissue. Some stylets may also have a blunt tip that prevents coring by the introducer needle but without the cutting tip.

Once the target is reached, the stylet can be removed in preparation for the specific intervention, for example, insertion of a biopsy device.

The process of guiding the introducer needle to the target is often aided by CT imaging which can provide an image showing the target and helping visualize and align the needle with the target. The CT machine may further provide a laser guide aligned with the image slice providing a reference against which the needle angle may be compared.

While CT imaging can help in guiding the needle, the material of the needle (often a metal such as stainless steel) and its length can result in severe image artifacts at the needle tip extending along the needle axis and can substantially block x-ray transmission along rays aligned with the needle. This artifact is positioned to obscure the region of greatest interest in guiding the tip of the needle around a critical structure and to a location within the lesion or other target.

Image artifacts in computed tomography arise from the underlying mathematical process that is used to develop cross-sectional slice images from attenuation (projection) data collected edgewise through the slices. A condition of this reconstruction process is that each voxel in the imaged volume be illuminated over a range of angles in excess of 180° plus the angle subtended by the x-ray beam in the imaging plane. The needle material causes x-ray photon starvation at certain angles in this required range. The result is a reconstruction artifact manifest as a dark streak extending from the tip of the needle along axis of the needle. These same artifacts can occur with other slender interventional probes including ablation electrodes and the like. Henceforth these needles, electrodes and similar medical devices for percutaneous insertion into the body will be collectively referred to as "probes".

Current approaches to reducing artifacts caused by photon starvation may attempt to estimate missing x-ray attenuation values; however, estimation can introduce additional errors into the image. These techniques may not be practical for real-time imaging or may require additional features such as dual energy imaging that are not found in many x-ray machines.

SUMMARY OF THE INVENTION

The present invention provides a tomographic x-ray machine that acquires tomographic projection data in an acquisition plane that is angled with respect to a plane holding the insertion axis of the probe and the target within the patient. This angulation decreases the length and size of the image artifact aligned with the probe and proximate to the tip in an image plane holding the probe. This ability to acquire the data at an angle with respect to the plane of the probe is possible because of the small amount of angulation required that is compatible with imaging volume provided in current multislice CT machines. Several methods for identifying of the probe trajectory on which the angulation is based are provided, permitting automatic gantry angulation and, in some embodiments, permitting dynamic adjustment of the angulation of the acquisition plane and repositioning of the CT couch during the probe insertion, further improving probe visualization.

More specifically, and in one embodiment, the invention provides an x-ray imaging machine having an x-ray source and x-ray detector opposed along an x-ray axis and supported to orbit in opposition about a rotational axis to collect tomographic projection data with respect to an acquisition plane perpendicular to the rotational axis, the tomographic projection data comprising measured x-ray attenuation along multiple rays over a range of rotational angles. The x-ray imaging machine also includes an image display and a tomography control processor receiving the tomographic projections data. The tomography control processor operates to (a) receive data defining, within a trajectory plane, a probe insertion trajectory along which a probe will be inserted; (b) position the rotational axis of the x-ray source and x-ray detector to tilt the acquisition plane; (c) reconstruct the tomographic projection data into an image aligned with the trajectory planes; (d) display the image on the image display; and (e) repeat (b)-(e) during a probe insertion interval.

It is thus a feature of at least one embodiment of the invention to reduce image artifacts in the critical area of the probe tip aligned with the probe trajectory by using an angled acquisition plane.

The x-ray imaging machine may further include a patient support, and the data defining the probe insertion trajectory may include a probe target location with respect to the patient support. In this case, the tomographic control processor may also determine a necessary positioning of the patient support to automatically place the probe target location within an intersection between the trajectory plane and an acquisition volume about the acquisition plane.

It is thus a feature of at least one embodiment of the invention to ensure that the artifact-reducing angulation maintains a positioning of the patient allowing acquisition of relevant data for imaging the trajectory of the probe.

In some embodiments, the input describing probe trajectory includes identification of a puncture point, where the probe is inserted through skin of the patient, and a target point for the probe tip. The tomographic control processor may then control the patient support and the tilt so that the acquisition volume around the acquisition plane subtends the distance between the puncture point and the target point.

It is thus a feature of at least one embodiment to provide an initial reduced artifact image fully covering the relevant trajectory of the probe insertion from skin to target.

The tomographic control processor may position the rotational axis to be about 6° (or generally between 3° and 30°) from a normal to the trajectory plane.

It is thus a feature of at least one embodiment of the invention to provide substantial artifact reduction within a range of angulations achievable with current x-ray systems and acquisition volumes.

The x-ray imaging machine may further receive a probe target location within the patient, and the tomographic control processor may receive data indicating progress of the probe along the probe insertion trajectory and operate to change the tilt of the acquisition plane with respect to the trajectory plane as a function of probe insertion depth, increasing the tilt between the rotational axis and a normal to the trajectory plane as the probe approaches the target.

It is thus a feature of at least one embodiment of the invention to adjust acquisition plane tilt dynamically to effect a trade-off between artifact reduction and trajectory path visualization length, imaging a greater length at the beginning of the probe insertion and near the end of probe insertion providing a greater reduction in image artifact.

The data indicating progress of the probe along the probe insertion axis may be obtained by processing of the image to monitor the position of the probe with respect to at least one of insertion depth and angle. In an alternative or additional embodiment, a sensor may be mechanically attached to the probe indicating either or both of insertion depth and angle.

It is thus a feature of at least one embodiment of the invention to provide an automatic method of monitoring probe insertion depth to implement this dynamic tilt control.

The data defining the probe insertion trajectory may be obtained from at least one of an initial alignment of the acquisition plane and the trajectory plane and a probe alignment guide (such as but not limited to a laser) positionable in alignment with the probe trajectory and providing sensors producing the data defining the probe insertion trajectory.

It is thus a feature of at least one embodiment of the invention to implement artifact reduction without the need for additional trajectory-defining steps or inputs by the physician.

The tomographic projection processor may monitor the trajectory of the probe in an acquisition volume around the acquisition plane to adjust the angles of the image plane according to changes in the monitored trajectory during probe insertion.

It is thus a feature of at least one embodiment of the invention to accommodate changes in the probe trajectory to adjust the imaging plane in addition to the acquisition plane as is done to minimize artifacts.

These particular objects and advantages may apply to only some embodiments falling within the claims and thus do not define the scope of the invention.

DETAILED DESCRIPTION OF THE PREFERRED EMBODIMENT

Figure 1:
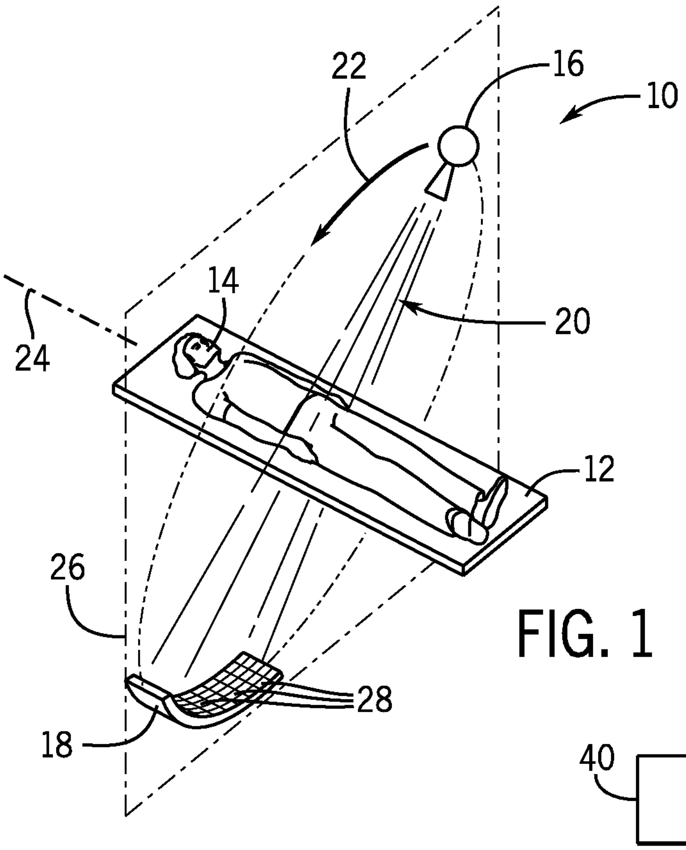
FIG. 1 is a simplified perspective view of an x-ray machine suitable for use with the present invention showing an x-ray source and x-ray detector that may rotate within an acquisition plane to collect tomographic data.

Referring now to FIG. 1, an x-ray machine 10 suitable for use with the present invention may provide a patient support 12 such as a radiolucent patient table upon which a patient 14 may be positioned. An x-ray source 16 and x-ray detector 18 may be mounted on a gantry (not shown in FIG. 1 for clarity) in opposition about the patient support 12 and positioned so that an x-ray beam 20 from the x-ray source 16 is directed toward the detector 18 through the patient support 12. As fixed in opposition, the x-ray source 16 and x-ray detector 18 may orbit the patient table as indicated by arrow 22 about a rotational axis 24 typically roughly directed along the craniocaudal axis of the patient 14. As so arranged, the x-ray source 16 and x-ray detector 18 rotate within an acquisition plane 26 normal to the rotational axis 24.

In one nonlimiting example, the x-ray machine 10 may be a medical computed tomography machine having a detector 18 for acquiring volumetric data over two-dimensionally arrayed detector elements 28. The detector elements 28, as so positioned, may each provide x-ray attenuation measurements along different individual rays of the x-ray beam 20 through the patient in a generally conical volume. When the gantry is rotated, the x-ray machine 10 may acquire a tomographic projections set of x-ray attenuation measurements collected at multiple different angles (projections) over a range of at least 180° plus the in-plane angular extent of the x-ray beam 20 within the acquisition plane 26. This tomographic projections set is sufficient to generate a slice image providing a cross-section along the acquisition plane 26.

Alternatively, the x-ray machine 10 may be any of a variety of x-ray devices capable of providing tomographic projections set acquisitions including, for example, C-arm type devices and the like and devices in which the x-ray source 16 and x-ray detector 18 are mounted on robotic arms.

Figure 2:
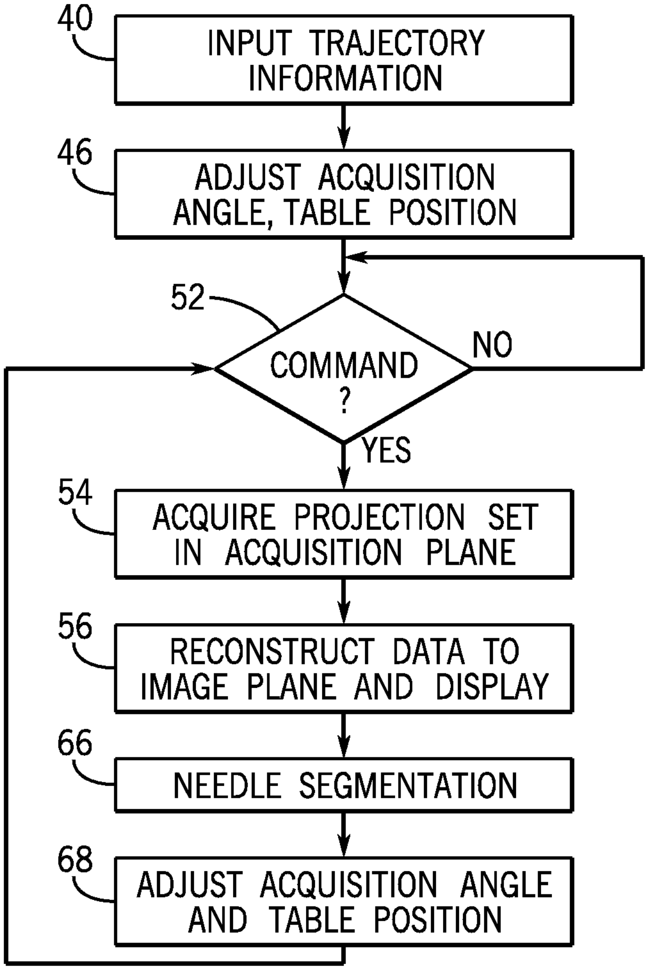
FIG. 2 is a flowchart describing the steps of the present invention in reducing probe-induced artifacts in an image produced by the x-ray machine of FIG. 1.
Figure 3A:
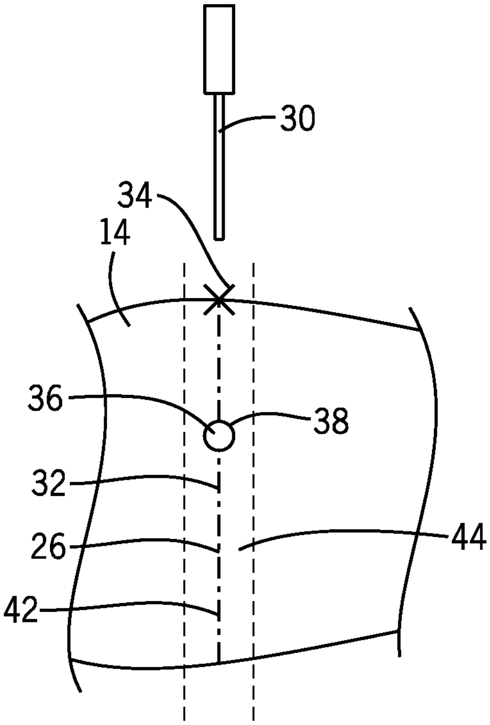
FIGS. 3*a* and 3*b* are side views in phantom of the patient showing a probe trajectory and an initial alignment of the image plane and acquisition plan (FIG. 3*a*) and subsequent tipping of the acquisition plane with respect to the image plane used in the present invention (FIG. 3*b*)
Figure 3B:
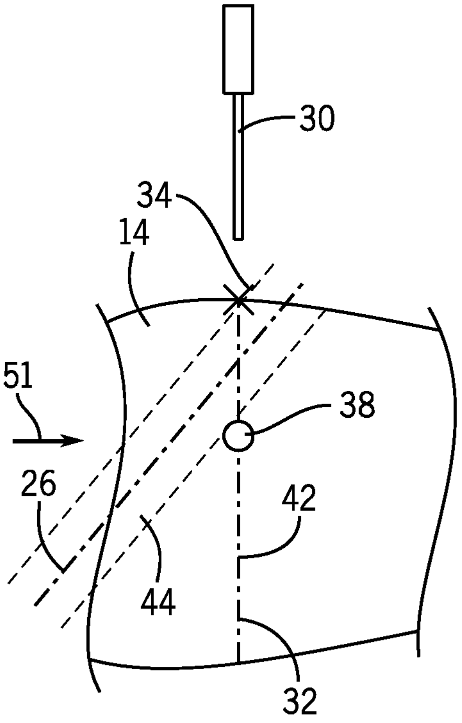
Figure 4:
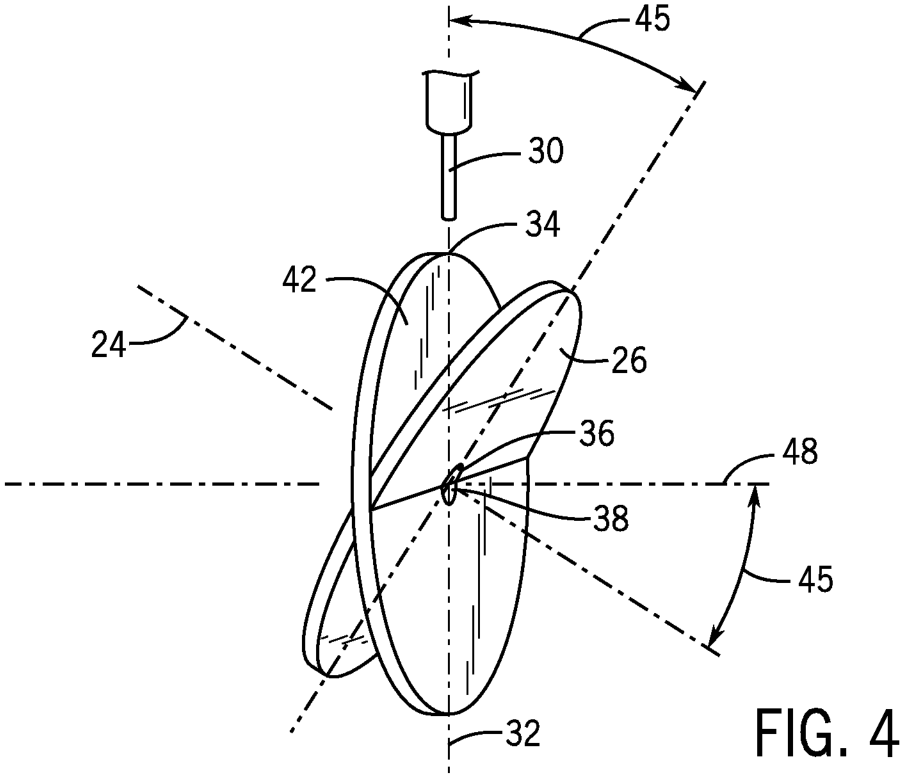
FIG. 4 is a geometric representation of the divergence between the image plane and the acquisition plane of FIG. 3 illustrating various angles and dimensions used in the description.

Referring now to FIGS. 2 and 3*a*, during an interventional procedure, a probe 30 may be inserted along a trajectory 32 of the probe 30 into the patient 14, the trajectory 32 extending from a puncture site 34 to a target 36, the latter at or within a lesion 38 or the like. Probes 30 suitable for use with the present invention are described in co-pending U.S. application Ser. No. 18/487,228 filed Nov. 21, 2023, and entitled "Introducer Needle and Stylet for Interventional Procedures," assigned to the assignee of the present application, and hereby incorporated by reference. More generally, the probe 30 may also be of conventional design constructed of materials that are substantially more x-ray absorbing than the surrounding tissue. Such materials include but are not limited to materials with an atomic number comparable to or greater than metals like stainless steel.

The trajectory 32 must be selected to avoid critical structures such as arteries or the like and, in this regard, it is desirable to be able to image the tip of the probe 30 as it moves along the trajectory 32 using computed tomography imaging of a slice encompassing the probe trajectory 32.

In realizing this goal and, as indicated by process block 40 of FIG. 2, in a first step, trajectory information defining the trajectory 32 is collected. In one embodiment this information may be provided as a coordinate of the puncture site 34 and of the target 36, for example, in three dimensional space, as referenced with respect to the patient support 12 presuming a previous registration of the patient 14 with those table coordinates as is understood in the art.

In one embodiment, this trajectory information may be collected by aligning the gantry holding the x-ray source 16 and x-ray detector 18 so that the acquisition plane 26 is aligned with the trajectory 32. This initial alignment may be facilitated, for example, using an alignment laser (not shown) frequently provided with the x-ray machine 10 demarcating the acquisition plane 26. In addition or alternatively, this alignment may be confirmed by an initial tomographic acquisition in this position with the probe 30 removed to eliminate artifacts.

Alternatively, the information describing the trajectory 32 is provided with respect to pre-procedure images obtained of the patient 14, where the puncture site 34 and target 36 are identified on those images and then matched to table position during a registration of the patient 14. This determination of the trajectory 32 may be done by viewing a three-dimensional volume of pre-procedure images or by viewing two-dimensional images.

Other methods of determining this trajectory information with respect to the patient and table will be described further below.

As noted, the information describing the trajectory 32 will be used to identify a desired image plane 42 containing the trajectory 32.

Referring now also to FIGS. 2, **3*b* and 4, once the information defining the trajectory 32 has been obtained, rotational axis 24 of the x-ray source 16 and detector 18 is adjusted to tip the acquisition plane 26 out of alignment with the image plane 42 and the trajectory 32 per process block 46. This degree of angulation 45 will typically be at least 3° and in some cases greater than 5°, for example 6°, but may be greater. In many situations, the degree of angulation 45 will be less than 30° and in some cases less than 10°. This angulation describes an angle between the image plane 42 and acquisition plane 26 or between a surface normal 48 of the image plane 42 and the rotational axis 24 of acquisition plane 26. Note that the image plane 42 need not be and will typically not be a 0° angular gantry tilt with respect to the table axis. Generally, the acquisition plane 26 is, as mentioned above, the rotational plane of the x-ray source 16 and detector 18**.

As indicated in FIG. **3*b*, this angulation will be accompanied with a table motion 51 to retain a region of interest of the trajectory 32 within an acquisition volume 44 about the acquisition plane 26. The acquisition volume 44 defines voxels that can be reconstructed for a given angulation of the acquisition plane 26. Initially, this region of interest of the trajectory 32 will be the entire length between the puncture site 34 and the target 36**.

As indicated by decision block 52, upon command by the physician performing the procedure, the x-ray machine 10 then acquires a projection set along the tipped acquisition plane 26, typically but not necessarily with a single gantry rotation. This data set typically includes the puncture site and target.

At succeeding process block 56, the data so acquired is reconstructed into an image aligned with the image plane 42. This is contrary to a typical reconstruction of an image that is aligned with the acquisition plane 26. The process of making this image reconstruction that is angled with respect to the acquisition plane 26 may, in one example, reconstruct the data within the acquisition plane 26 to a set of voxels and then select and assemble the voxel aligned with the image plane 42. A nonlimiting technique for this transformation is described, for example, in Defrise M, Noo F, Kudo H, Rebinning-Based Algorithms for Helical Cone-Beam CT, Phys Med Biol. 2001 November;46 (11):2911-37, doi: 10.1088/0031-9155/46/11/311, PMID: 11720355, hereby incorporated by reference.

This image reconstructed in the image plane 42 that holds the trajectory 32 is then displayed to the physician to confirm the location of the probe 30 along the trajectory 32 with respect to other body structures, including the target 36.

Figure 5:
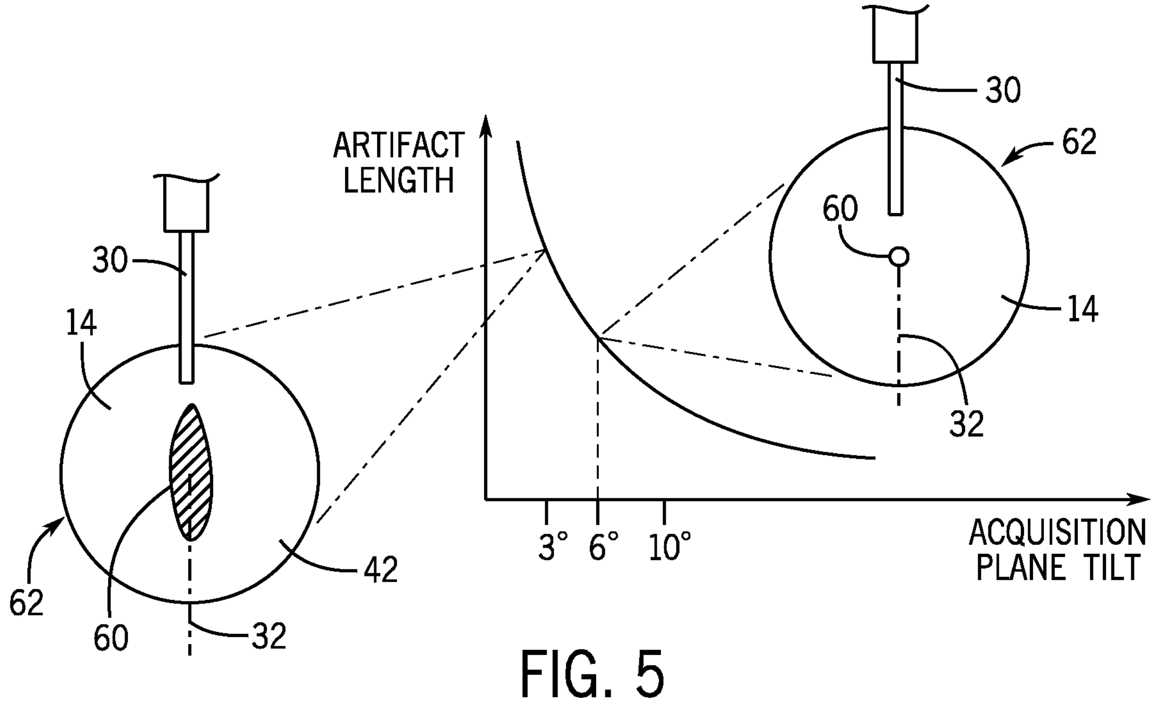
FIG. 5 is a plot of artifact length versus tip angle with depictions of a reduction in artifact at the tip of the probe along the trajectory of insertion as provided by the present invention.

Referring now to FIG. 5, the present inventors have determined that relatively small angulation of the acquisition plane 26 with respect to the image plane 42 substantially reduces a size of the image artifact 60 in an image 62 of the patient in the image plane 42. The size of the image artifact 60 is a rapidly decreasing function of the angulation of the acquisition plane 26 and thus can provide acceptable minimization of the image artifacts 60 at an angle of 6° with diminishing reductions thereafter. While the inventors do not wish to be bound by a particular theory, the reduction in the length and size of the artifact 60 appears to be driven by a reduced path length of x-rays through the material of the probe 30 with respect to voxels in the relevant area proximate to the tip of the probe 30.

Figure 6A:
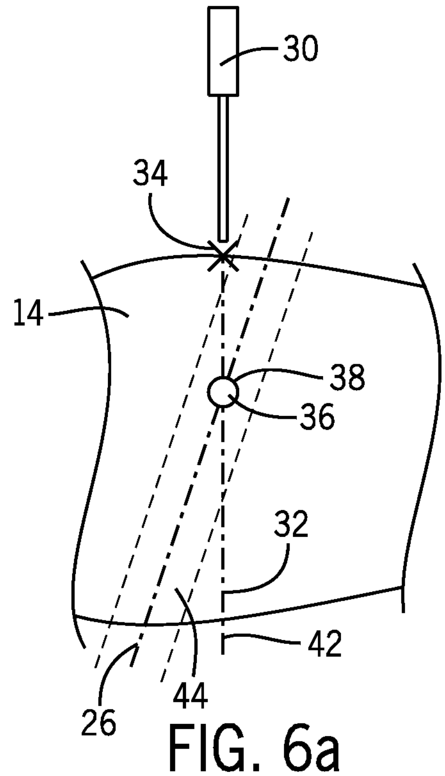
FIGS. 6*a* and 6*b* are figures similar to FIG. 3 showing the process of dynamically changing angulation as the probe progresses along the trajectory to further reduce image artifacts.
Figure 6B:
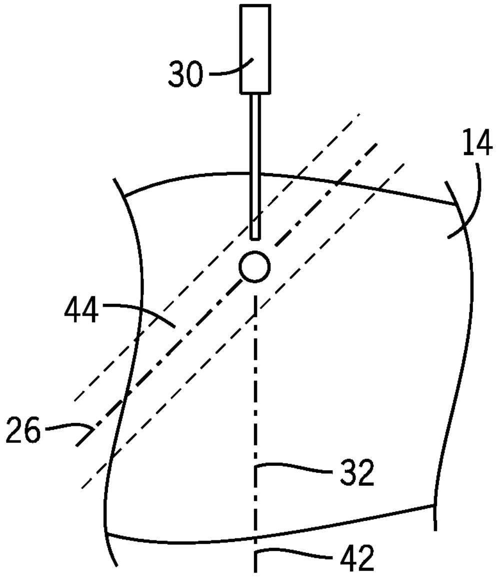

Referring now to FIGS. 2 and 6, as indicated by process block 66, the acquired data at process block 54 may optionally be reviewed to identify the location of the probe 30 using an automatic probe segmentation program of a type understood in the art. This information allows both a determination of change in the trajectory 32 of the probe 30 and a determination of the position of the tip of the probe 30 as it progresses along the trajectory 32. This information may be used at process block 68 for two purposes. The first is to make any adjustments to the positioning of the image plane 42 to ensure that displayed images of process block 56 contain the trajectory 32. These adjustments also make necessary adjustments in the acquisition plane 26, which are based on the trajectory 32.

Independent of whether the image plane 42 has changed, as indicated by FIGS. **6*a* and 6*b*, the changing position of the tip of the probe 30 may be used to change the relative angulation of the acquisition plane 26 with respect to the trajectory 32 and optionally the collimation of the x-ray beam 20. As previously noted, initially and as indicated in FIG. 6*a*, the angulation of the acquisition plane 26 with respect to the trajectory 32 and it's collimation may be such as to allow for a complete reconstruction of data along the trajectory of the probe 30 between the puncture 34 and the target 36. This information assists in initial insertion of the probe 30** in the proper direction.

As the probe 30 progresses along the trajectory, and as indicated in FIG. **6*b*, the angulation of the acquisition plane 26 may be increased (and necessary adjustments in the table position made) so that the acquired data does not fully span the trajectory 32 between the puncture site 34 and the target 36. This will result in an incomplete image in the image plane 42 but will provide additional attenuation of the image artifacts 60 at the relevant portions of the trajectory 32 between the tip of the probe 30 and the target 36. Optionally the collimation of the x-ray beam 20 may be changed either to be narrower consistent with the need to image less of the trajectory 32**, or wider offset the angulation depending on dose concerns.

In some embodiments, the missing data of the image plane 42 may be spliced from earlier data acquired, for example, in the imaging associated with FIG. 6*a*, or the size of the image may be simply decreased in radius.

Process blocks 54, 56, 66, 68 may be repeated as desired during the insertion of the probe 30 under control of the physician per decision block 52.

Figure 7:
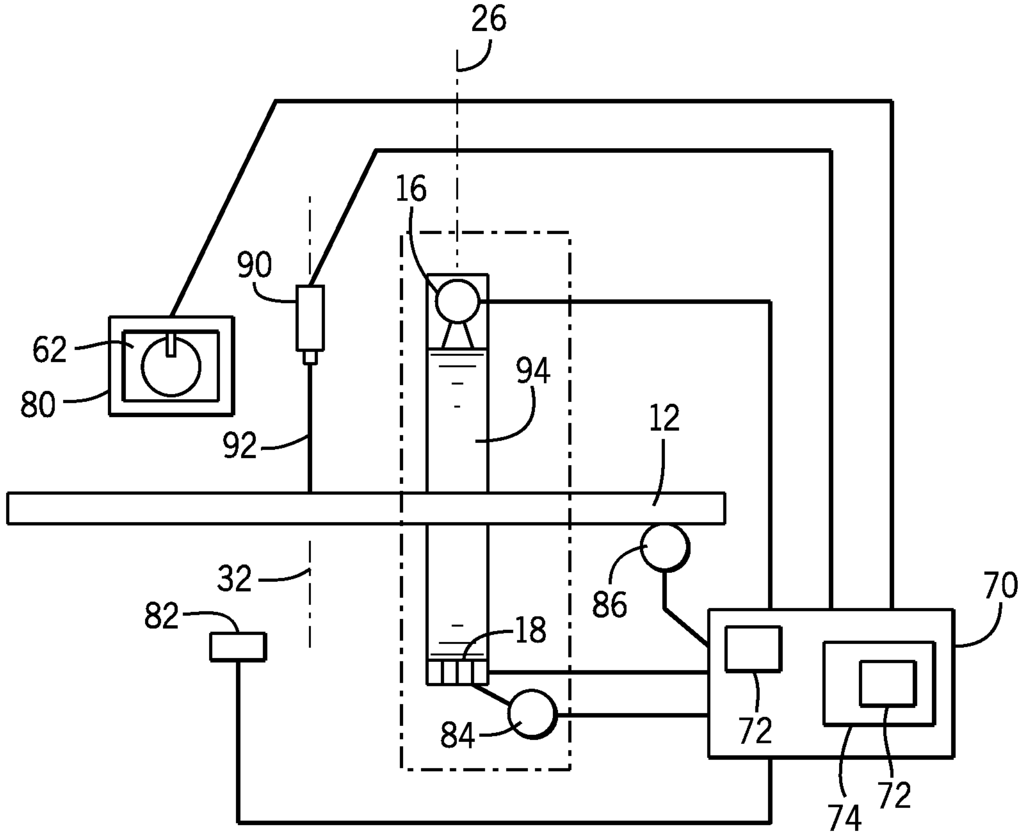
FIG. 7 is a functional block diagram of the x-ray machine of FIG. 1 showing interconnections between a tomographic processor and elements of the x-ray machine for automatic control according to the present invention, and further showing a laser probe insertion guide.

Referring now to FIG. 7, the various steps described in FIG. 2 may be implemented automatically using a programmable tomographic control processor 70 having one or more computer processors 72 communicating with electronic memory 74 holding a stored program 76. The stored program 76 may implement the steps of FIG. 2. For this purpose, the tomographic control processor 70 may communicate with a monitor 80 for displaying an image 62 taken along the image plane 42. Generally, the tomographic control processor 70 may also communicate with a foot switch 82 providing the commands at decision block 52 and with gantry control motors and sensors 84 controlling motion of the gantry 94 holding the x-ray source 16 and x-ray detector 18. Additional paths of communication to the tomographic control processor 70 allows a collecting and relaying of data from that x-ray detector 18 and the control of the x-ray source 16.

The tomographic control processor 70 may also communicate with table control actuators 86 to control motion of the patient support 12. In some embodiments, the tomographic control processor 70 may also perform the necessary calculations for image reconstruction generally known in the art.

In one embodiment, the x-ray machine 10 may provide a laser projector 90 that may be positioned independently of the data acquisition plane 26 to be aligned with the desired probe trajectory 32 offering the physician assistance in aligning the probe 30. This laser projector 90 may be fixed with respect to the patient support 12 or other stationary reference point. Sensors on the laser projector 90 may be used to provide the trajectory information at process block 40 of FIG. 2 as discussed above.

Figure 8:
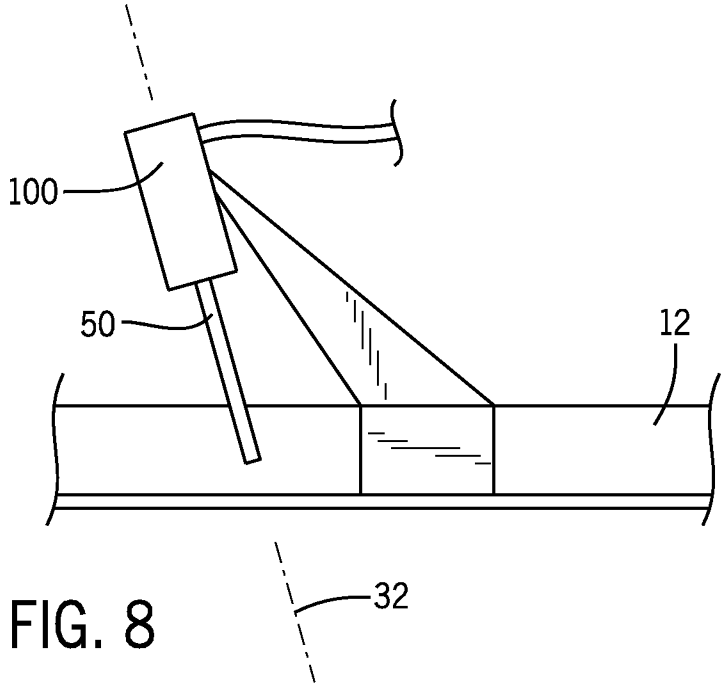
FIG. 8 is a fragmentary detail of an alternative insertion guide providing a mechanical connection to the probe that may be used together with or in lieu of the laser insertion guide of FIG. 7.

Referring now to FIG. 8, in an alternative embodiment, the information at process block 40 may be provided by a mechanical fixture 100 that may be angulated to hold the probe 30 at a desired angle for insertion along the probe trajectory 32 and instrumented to provide this information.

It will be generally understood that a tilting of the acquisition plane 26 with respect to the image plane 32 can be done by angulation of the gantry (with respect to the room) or by a similar angulation of the patient table 12 (with respect to the room) to produce the desired relative offset between the image plane 32 and the acquisition plane 26.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to a processor should be understood to include one or more processing devices that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. An x-ray imaging machine comprising:

an x-ray source and x-ray detector opposed along an x-ray axis and supported to orbit in opposition about a rotational axis to collect tomographic projection data with respect to an acquisition plane perpendicular to the rotational axis, the tomographic projection data comprising measured x-ray attenuation along multiple rays over a range of rotational angles;

an image display; and a tomography control processor receiving the tomographic projections data and operating to:

(a) receive data defining, within a trajectory plane, a probe insertion trajectory along which a probe will be inserted;

(b) position the rotational axis of the x-ray source and x-ray detector to tilt the acquisition plane with respect to the trajectory plane;

(c) acquire a tomographic projection set in the acquisition plane;

(d) reconstruct the tomographic projection data into an image aligned with the trajectory planes;

(e) display the image on the image display; and (f) repeat (c)-(e) during a probe insertion interval;

further including a patient support; and wherein the data defining the probe insertion trajectory provides a probe target location with respect to the patient support; and wherein the tomographic control processor determines a necessary positioning of the patient support to place the probe target location within an intersection between the trajectory plane and an acquisition volume about the acquisition plane; and wherein the data defining the probe insertion trajectory includes a puncture point where a probe is to be inserted through skin of the patient and a target point for the probe tip and wherein the tomographic control processor controls the patient support and the tilt so that the acquisition volume around the acquisition plane subtends a distance between the puncture point and the target point.

2. An x-ray imaging machine comprising:

an x-ray source and x-ray detector opposed along an x-ray axis and supported to orbit in opposition about a rotational axis to collect tomographic projection data with respect to an acquisition plane perpendicular to the rotational axis, the tomographic projection data comprising measured x-ray attenuation along multiple rays over a range of rotational angles;

an image display; and a tomography control processor receiving the tomographic projections data and operating to:

(a) receive data defining, within a trajectory plane, a probe insertion trajectory along which a probe will be inserted;

(b) position the rotational axis of the x-ray source and x-ray detector to tilt the acquisition plane with respect to the trajectory plane;

(c) acquire a tomographic projection set in the acquisition plane;

(d) reconstruct the tomographic projection data into an image aligned with the trajectory planes;

(e) display the image on the image display; and (f) repeat (c)-(e) during a probe insertion interval;

further including a patient support; and wherein the data defining the probe insertion trajectory provides a probe target location with respect to the patient support; and wherein the tomographic control processor determines a necessary positioning of the patient support to place the probe target location within an intersection between the trajectory plane and an acquisition volume about the acquisition plane; and wherein the tomographic control processor positions the rotational axis to be greater than 3° from a normal to the trajectory plane.

3. The x-ray imaging machine of claim 2 wherein the data defining the probe insertion trajectory is obtained from at least one of an initial alignment of the acquisition plane and the trajectory plane and a probe alignment guide positionable in alignment with the trajectory of the probe and providing sensors producing the data defining the probe insertion trajectory.

4. The x-ray imaging machine of claim 2 wherein the probe insertion interval is defined by operator-initiated scan requests during which a tomographic projections set is acquired.

5. The x-ray imaging machine of claim 2 wherein the image is produced solely with data acquired in the acquisition plane.

6. The x-ray imaging machine of claim 3 wherein the probe alignment guide is a laser projecting an alignment beam along the trajectory of the probe positionable independently of the rotation axis.

7. An x-ray imaging machine comprising:

an x-ray source and x-ray detector opposed along an x-ray axis and supported to orbit in opposition about a rotational axis to collect tomographic projection data with respect to an acquisition plane perpendicular to the rotational axis, the tomographic projection data comprising measured x-ray attenuation along multiple rays over a range of rotational angles;

an image display; and a tomography control processor receiving the tomographic projections data and operating to:

(a) receive data defining, within a trajectory plane, a probe insertion trajectory along which a probe will be inserted;

(b) position the rotational axis of the x-ray source and x-ray detector to tilt the acquisition plane with respect to the trajectory plane;

(c) acquire a tomographic projection set in the acquisition plane;

(d) reconstruct the tomographic projection data into an image aligned with the trajectory planes;

(e) display the image on the image display; and (f) repeat (c)-(e) during a probe insertion interval; and further including a patient support; and wherein the probe insertion trajectory provides a probe target location within the patient and with respect to the patient support; and wherein the tomographic control processor receives data indicating progress of the probe along the probe insertion trajectory and operates to change the tilt of the acquisition plane with respect to the trajectory plane as a functional of probe insertion depth, increasing the tilt between the rotational axis and a normal to the trajectory plane as the probe approaches the target.

8. The x-ray imaging machine of claim 7 wherein the data indicating progress of the probe along the probe insertion axis is obtained from at least one of a processing of the image to monitor the position of the probe and a sensor mechanically attached to the probe, both indicating at least one of insertion depth and angle.

9. An x-ray imaging machine comprising:

an x-ray source and x-ray detector opposed along an x-ray axis and supported to orbit in opposition about a rotational axis to collect tomographic projection data with respect to an acquisition plane perpendicular to the rotational axis, the tomographic projection data comprising measured x-ray attenuation along multiple rays over a range of rotational angles;

an image display; and a tomography control processor receiving the tomographic projections data and operating to:

(a) receive data defining, within a trajectory plane, a probe insertion trajectory along which a probe will be inserted;

(b) position the rotational axis of the x-ray source and x-ray detector to tilt the acquisition plane with respect to the trajectory plane;

(c) acquire a tomographic projection set in the acquisition plane;

(d) reconstruct the tomographic projection data into an image aligned with the trajectory planes;

(e) display the image on the image display; and (f) repeat (c)-(e) during a probe insertion interval; and wherein the tomographic projection processor monitors the trajectory of the probe in an acquisition volume around the acquisition plane to adjust the angles of the image plane according to changes in the monitored trajectory during probe insertion.

10. A method of guiding a probe to a target within patient tissue employing a tomographic imaging on a CT machine providing an x-ray source and x-ray detector opposed along an x-ray axis and supported to orbit in opposition about a rotational axis to collect tomographic projection data with respect to an acquisition plane perpendicular to the rotational axis, the tomographic projection data comprising measured x-ray attenuation along multiple rays over a range of rotational angles and an image display, the method comprising:

(a) receiving data defining, within a trajectory plane, a probe insertion trajectory along which a probe will be inserted;

(b) positioning the rotational axis of the x-ray source and x-ray detector to tilt the acquisition plane with respect to the image plane by an amount according to the data defining the trajectory plane;

(c) acquiring a tomographic projection set in the acquisition plane;

(d) reconstructing tomographic projection data into an image aligned with the trajectory planes;

(e) displaying the image on an image display; and (f) repeating (c)-(e) while guiding the probe along the trajectory;

further including a patient support; and wherein the data defining the probe insertion trajectory provides a probe target location with respect to the patient support; and wherein the tomographic control processor determines a necessary positioning of the patient support to place the probe target location within an intersection between the trajectory plane and an acquisition volume about the acquisition plane; and wherein the tomographic control processor positions the rotational axis to be greater than 3° from a normal to the trajectory plane.

11. The method of claim 10 wherein the data describing the probe insertion trajectory includes a puncture point where a probe is to be inserted through skin of the patient and a target point for the probe tip and further including controlling the patient support and the tilt so that an acquisition volume around the acquisition plane subtends a distance between the puncture point and the target point.

12. The method of claim 10 wherein the probe insertion trajectory provides a probe target location within a patient and with respect to the patient support; and further including receiving data indicating progress of the probe along the probe insertion trajectory and changing the tilt of the acquisition plane with respect to the trajectory plane as a function of probe insertion depth to increase the tilt between the rotational axis and a normal to the trajectory plane as the probe approaches the target.

13. The method of claim 10 wherein the data defining the probe insertion trajectory is obtained from at least one of an initial alignment of the acquisition plane and the trajectory plane and a probe alignment guide positionable in alignment with the trajectory of the probe and providing sensors producing the data defining the probe insertion trajectory.

14. The method of claim 10 wherein the probe insertion interval is defined by operator-initiated scan requests during which a tomographic projections set is acquired.

15. The method of claim 10 including monitoring the trajectory of the probe in an acquisition volume around the acquisition plane to adjust the angle of the image plane according to changes in the monitored trajectory during probe insertion.

16. The method of claim 12 wherein the data indicating progress of the probe along the probe insertion axis is obtained from at least one of a processing of the image to monitor the position of the probe and a sensor mechanically attached to the probe indicating its insertion depth.

* * * * *